United States Patent [19]

Takahashi et al.

[11] 4,309,562

[45] Jan. 5, 1982

[54] HERBICIDAL COMPOUND, HERBICIDAL COMPOSITION CONTAINING THE SAME, AND METHOD OF USE THEREOF

[75] Inventors: Ryohei Takahashi, Kusatsu; Kanichi Fujikawa, Kyoto; Isao Yokomichi, Kusatsu; Sinzo Someya, Kusatsu; Nobuyuki Sakashita, Kusatsu, all of Japan

[73] Assignee: Ishihara Sangyo Kaisha, Ltd., Osaka, Japan

[21] Appl. No.: 788,068

[22] Filed: Apr. 15, 1977

Related U.S. Application Data

[62] Division of Ser. No. 596,784, Jul. 17, 1975.

[30] Foreign Application Priority Data

Jul. 17, 1974 [JP] Japan .................................. 49-82403
Jul. 17, 1974 [JP] Japan .................................. 49-82404
Oct. 14, 1974 [JP] Japan ................................ 49-117047

[51] Int. Cl.$^3$ ...................... C07C 69/76; A01N 37/38
[52] U.S. Cl. ........................................ 71/108; 560/62; 260/455 R; 260/544 R; 260/544 P; 544/71; 546/304; 548/266; 564/171; 564/169; 564/150; 564/155; 71/109; 562/471
[58] Field of Search .......................... 560/62; 562/471; 71/108, 109

Primary Examiner—Paul J. Killos
Attorney, Agent, or Firm—Sughrue, Mion, Zinn, Macpeak and Seas

[57]  ABSTRACT

α[4-(4-Trifluoromethylphenoxy)phenoxy]alkanecarboxylic acids (the "4-trifluoromethylphenoxy group" of which may contain one chlorine atom as a substituent) and derivatives thereof useful as a herbicide, a herbicidal composition containing the compound, methods of controlling weeds and production thereof.

6 Claims, No Drawings

HERBICIDAL COMPOUND, HERBICIDAL COMPOSITION CONTAINING THE SAME, AND METHOD OF USE THEREOF

This is a division of application Ser. No. 596,784, filed July 17, 1975.

BACKGROUND OF THE INVENTION

1. Field of the Invention

This invention relates to a novel compound useful as a herbicide for agriculture and horticulture, to a herbicidal composition containing the same, and to methods of controlling weeds and production thereof.

2. Description of the Prior Art

In recent years, a number of herbicides have been developed and put into practical use. These herbicides have contributed to a saving of labor and an increased production in agriculture. However, there is still room for improvement, and novel chemicals which have reduced effects on useful cultivated plants but have a strong herbicidal action on undesirable plants and which are very safe in regard to environmental pollution have been desired. For example, phenoxyalkanecarboxylic acids represented by 2,4-dichlorophenoxyacetic acid, which have been known for a long time, have superior controlling effects on broad-leafed weeds and still find widespread use. However, since phenoxyalkanecarboxylic acids have only a slight activity on gramineous weeds which are the main noxious weeds, and are phytotoxic to broad-leafed plants which embrace many crops and cultivated trees, these chemicals have only a limited application. Diphenyl ethers represented by 2,4-dichloro-4'-nitrodiphenyl ether have recently gained wide acceptance, but their property of selectively exterminating noxious weeds is not sufficient. The 4-phenoxy-phenoxyalkanecarboxylic acids proposed recently in West German Patent Application No. P2223894/1972 exhibit some degree of improvement in selectivity, but suffer from the defect that their herbicidal activity is not sufficient.

SUMMARY OF THE INVENTION

The present invention provides an α-[4-(4-trifluoromethylphenoxy)phenoxy]alkanecarboxylic acid or a derivative thereof represented by the general formula (I):

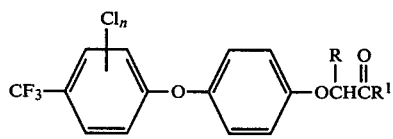

wherein R is a straight or branched chain $(C_1-C_6)$alkyl group with a methyl group being preferred; $R^1$ is a hydroxy group; an unsubstituted or substituted $(C_1-C_9)$alkoxy group, in which the alkyl moiety thereof may be straight or branched chain and in which the substituents may be one or more of a halogen atom, a hydroxy group, a trifluoromethyl group, a straight or branched chain $(C_1-C_4)$alkyl group or an alkoxy group containing a straight or branched chain $(C_1-C_4)$alkyl moiety, with a $(C_1-C_4)$alkoxy group being preferred; a $(C_1-C_4)$alkoxy-$(C_1-C_4)$alkoxy group, in which each of the alkyl moieties thereof may be straight or branched chain and in which the substituents may be one or more of a halogen atom, a hydroxy group, a trifluoromethyl group, a straight or branched chain $(C_1-C_4)$alkyl group or an alkoxy group containing a straight or branched chain $(C_1-C_4)$alkyl moiety, with a $C_2H_5OC_2H_4OC_2H_4O$-group being preferred; a $(C_1-C_4)$alkylthio group, in which the alkyl moiety thereof may be straight or branched chain, with a $(C_1-C_3)$alkylthio group being preferred; a $(C_2-C_4)$alkenyloxy group with an allyloxy group being preferred; a $(C_2-C_4)$alkynyloxy group with a propargyloxy group being preferred; a $(C_3-C_6)$cycloalkoxy group in which the cycloalkyl moiety thereof may be substituted with one or more of a halogen atom, a hydroxy group, a trifluoromethyl group, a straight or branched chain $(C_1-C_4)$alkyl group or an alkoxy group containing a straight or branched chain $(C_1-C_4)$alkyl moiety, with a cyclohexyloxy group which may be substituted with a methyl group being preferred; a phenoxy group in which the aryl moiety thereof may be substituted with one or more of a halogen atom, a hydroxy group, a trifluoromethyl group, a straight or branched chain $(C_1-C_4)$alkyl group or an alkoxy group containing a straight or branched chain $(C_1-C_4)$alkyl moiety; a phenylthio group in which the aryl moiety thereof may be substituted with one or more of a halogen atom, a hydroxy group, a trifluoromethyl group, a straight or branched chain $(C_1-C_4)$alkyl group or an alkoxy group containing a straight or branched chain $(C_1-C_4)$alkyl moiety; a benzyloxy group in which the aryl moiety thereof may be substituted with one or more of a halogen atom, a hydroxy group, a trifluoromethyl group, a straight or branched chain $(C_1-C_4)$alkyl group or an alkoxy group containing a straight or branched chain $(C_1-C_4)$alkyl moiety; an amino group; a mono-$(C_1-C_4)$alkylamino group, in which the alkyl moiety thereof may be straight or branched chain and may be substituted with one or more of a hydroxy group or a carboxy group, with a mono-$(C_1-C_3)$alkylamino group being preferred; a di-$(C_1-C_4)$alkylamino group, in which each of the alkyl moieties may be straight or branched chain, with a di-$(C_1-C_3)$alkylamino group being preferred; a hydrazino group; an N', N'-di-$(C_1-C_4)$-alkylhydrazino group in which the alkyl moieties thereof may be straight or branched chain; an anilino group in which the aryl moiety thereof may be substituted with one or more of a halogen atom, a hydroxy group, a trifluoromethyl group, a straight or branched chain $(C_1-C_4)$alkyl group or an alkoxy group containing a straight or branched chain $(C_1-C_4)$alkyl moiety; an N-$(C_1-C_4)$-alkyl-N-(phenyl)amino group in which the alkyl moiety thereof may be straight or branched chain and in which the aryl moiety thereof may be substituted with one or more of a halogen atom, a hydroxy group, a trifluoromethyl group, a straight or branched chain $(C_1-C_4)$alkyl group or an alkoxy group containing a straight or branched chain $(C_1-C_4)$alkyl moiety; a benzylamino group in which the aryl moiety thereof may be substituted with one or more of a halogen atom, a hydroxy group, a trifluoromethyl group, a straight or branched chain $(C_1-C_4)$alkyl group or an alkoxy group containing a straight or branched chain $(C_1-C_4)$alkyl moiety; a carbamoylamino group in which the N'-position thereof may be substituted with one or more of a straight or branched chain $(C_1-C_4)$alkyl group; an N-(halophenyl)carbamoylamino group in which the N'-position thereof may be substituted with one or more of a straight or branched chain $(C_1-C_4)$alkyl group or an alkoxy group containing a straight or branched chain $(C_1-C_4)$alkyl moiety, with an

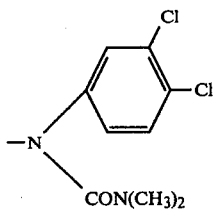

group being preferred;
a ($C_1$-$C_6$)acylamino group with an —NHCOCH$_3$ group being preferred;
an N-(halophenyl-N-($C_1$-$C_6$)acylamino group with an

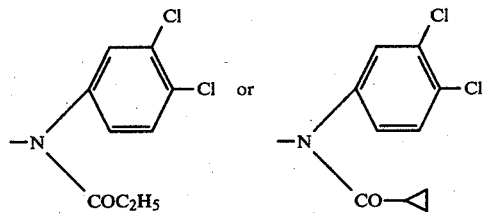

group being preferred; an amino group substituted with a heterocyclic group in which the heterocyclic moiety thereof may be substituted with one or more of a halogen atom or a straight or branched chain ($C_1$-$C_4$)alkyl group with an

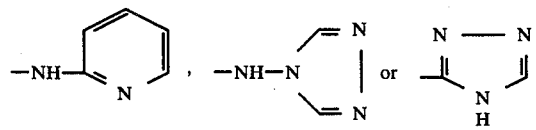

group being preferred; a cyclic amino group; an —OM group where M is a cation such as an alkali metal atom, an alkaline earth metal atom, or an ammonium group optionally substituted with an alkyl group or a substituted alkyl group; or a halogen atom; and n is 0 or 1; useful as a herbicidal compound.

The invention further provides a herbicidal composition comprising a herbicidally effective amount of at least one compound of the above general formula (I) and agriculturally acceptable adjuvants.

Still further, the invention provides a method for controlling weeds comprising applying a herbicidally effective amount of the above herbicidal composition to the weeds.

Also, the invention provides a method of producing the compounds of the general formula (I) above.

DETAILED DESCRIPTION OF THE INVENTION

The compound of the formula (I) of this invention useful as a herbicide (hereinafter, "herbicidal compound") contains a phenoxyalkanecarboxylic acid structure and a diphenyl ether structure in the molecule, and from a chemical structural standpoint might appear to be similar to the known herbicidal compounds described hereinabove, i.e., phenoxyalkanecarboxylic acids (e.g., as disclosed in Japanese Patent Publication No. 5548/54) and diphenyl ethers (e.g., as disclosed in U.S. Pat. No. 3,231,358). However, the herbicidal compound of the formula (I) is a novel compound, and has a unique herbicidal activity which differs from the herbicidal activities of these known types of herbicidal compounds. The herbicidal compound of this invention has the following two important characteristics.

(1) The compound of the formula (I) has a strong selective herbicidal activity toward gramineous plants which is much stronger than that of known diphenyl ethers. On the other hand, since the compound affects broad-leafed plants to only a slight extent, especially those which have grown to some extent, it can be used with high safety on broad-leafed crops or cultivated trees. In other words, the compound of this invention has quite a reverse selectivity to and far higher selectivity than the known phenoxyalkanecarboxylic acids.

(2) The compound of the formula (I) has great translocatability in the plant structure. The compound is absorbed by the foliage and roots of a plant, and mainly causes a decay of meristematic cells in the nodes, which leads to a withering, falling down and death of the plant. Accordingly, even when applied only to a very limited part of the plant structure, the compound exhibits a strong herbicidal activity, and weeds which have grown considerably are withered and killed due to the activity of the compound of this invention. Such activity is not observed in known diphenyl ethers.

In the definitions with respect to the formula (I) representing the herbicidal compound of this invention, suitable halogen atoms include bromine, chlorine, fluorine and iodine atoms with a chlorine atom being preferred, suitable straight or branched chain ($C_1$-$C_4$)alkyl groups include methyl, ethyl, propyl, iso-propyl, n-butyl, sec-butyl and tert-butyl groups with a methyl group or an ethyl group being preferred, and suitable ($C_1$-$C_4$)alkoxy groups are those containing as moieties the alkyl groups described above which may be straight or branched chain, with a methoxy group or an ethoxy group being preferred. The term "cyclic amino group" as used herein means those groups containing a nitrogen atom in the ring with the nitrogen atom having the function of the nitrogen atom of an amino group, such as a morpholino or piperidino group with a morpholino group being preferred. The term "cation" for M means, for example, an alkali metal atom such as sodium or potassium, an alkaline earth metal atom such as calcium or magnesium, or an ammonium group optionally substituted with a straight or branched chain ($C_1$-$C_4$)alkyl group such as a methyl or ethyl group, or a straight or branched chain ($C_1$-$C_4$)alkyl group substituted with, for example, a hydroxy group. Further, the carboxy groups described herein may be in the form of a free carboxy group of the formula —COOH, a salt of a carboxy group of the formula —COOM wherein M is as defined above, or an ester of a carboxy group of the formula —COO-($C_1$-$C_4$)alkyl in which the alkyl moiety thereof may be straight or branched chain.

Suitable examples of the derivatives of the α-[4-(4-trifluoromethylphenoxy)phenoxy]alkanecarboxylic acid as set forth previously, other than the above, include, for example, an acid anhydride of an α-[4-(4-trifluoromethylphenoxy)phenoxy]-alkanecarboxylic acid, a polyester formed between the above-described acid and a polyol such as ethylene glycol, etc., and the like.

The herbicidal compound of the formula (I) can be used commercially as an active ingredient of herbicidal compositions, as will be seen from the Test Examples given hereinafter. Of the herbicidal compounds of the invention, those represented by the following formula (I'):

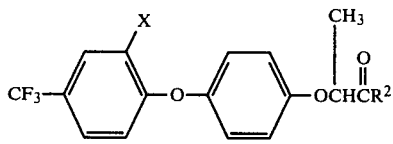

are preferred, and those represented by the following general formula (I"):

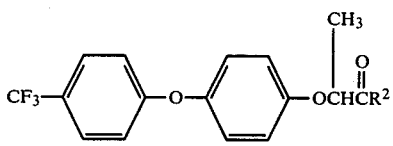

are especially preferred. In the above formulae (I') and (I") X is a hydrogen atom or a chlorine atom, and $R^2$ is a hydroxy group, an unsubstituted or substituted ($C_1$-$C_9$)alkoxy group, as described for $R^1$, a ($C_1$-$C_4$)alkoxy-($C_1$-$C_4$)alkoxy group as described for $R^1$, a ($C_1$-$C_4$)alkylthio group, a ($C_2$-$C_4$)alkenyloxy group, an unsubstituted or substituted ($C_3$-$C_6$)cycloalkoxy group as described for $R^1$, an unsubstituted or substituted phenoxy group as described for $R^1$, an unsubstituted or substituted benzyloxy group as described for $R^1$, an amino group, an unsubstituted or substituted mono-($C_1$-$C_4$)alkylamino group as described for $R^1$, a di-($C_1$-$C_4$)alkylamino group, a hydrazino group, an N',N'-di-($C_1$-$C_4$)alkylhydrazino group in which the alkyl moieties thereof may be straight or branched chain, an unsubstituted or substituted anilino group as described for $R^1$, an unsubstituted or N'-substituted carbamoylamino group as described for $R^1$, a ($C_1$-$C_6$)acylamino group, an amino group substituted with an unsubstituted or substituted heterocyclic group as described for $R^1$, or an —OM group wherein M is as defined above.

Particularly preferred compounds of this invention are those of the general formulae (I') and (I") above wherein $R^2$ is a hydroxy group; a ($C_1$-$C_9$)alkoxy group in which the alkyl moiety thereof may be straight or branched chain; a ($C_1$-$C_4$)alkoxy-($C_1$-$C_4$)alkoxy group; a ($C_1$-$C_4$)alkoxy-($C_1$-$C_4$)alkoxy-($C_1$-$C_4$)alkoxy group; an alkylthio group containing a straight or branched chain ($C_1$-$C_4$)alkyl moiety; a ($C_2$-$C_4$)alkenyloxy group; a cyclohexyloxy group in which the cyclohexyl moiety thereof may be substituted with a methyl group; a phenoxy group in which the aryl moiety thereof may be substituted with one or more of a halogen atom, a methyl group or a methoxy group; a benzyloxy group; an amino group; a mono-($C_1$-$C_4$)alkylamino group in which the alkyl moiety thereof may be straight or branched chain and may be substituted with a carboxy group; a di-($C_1$-$C_4$)alkylamino group in which the alkyl moiety thereof may be straight or branched chain; a hydrazino group; an N',N'-di-($C_1$-$C_4$)alkylhydrazino group in which the alkyl moieties thereof may be straight or branched chain; an unsubstituted or substituted anilino group as described for $R^1$; a carbamoylamino group in which the N' position thereof may be substituted with one or more of a straight or branched chain ($C_1$-$C_4$)alkyl group; a ($C_1$-$C_4$)acylamino group; an N-pyridylamino group in which the pyridyl moiety thereof may be substituted with a methyl group; an N-triazolylamino group; a morpholino group; or an —O-M group wherein M is as defined above.

Typical examples of compounds of the formula (I) are given below.

| Compound No. | $Cl_n$ | R | $R^1$ | Melting Point (°C.) | Boiling Point (°C.) | Refractive Index |
|---|---|---|---|---|---|---|
| 1 | — | —$CH_3$ | —OH | 138–140 | — | — |
| 1' | — | —$CH_3$ | —OH | 117.5–118.5 (d-isomer) | — | — |
| 2 | — | —$CH_3$ | —ONa | — | — | — |
| 3 | — | —$CH_3$ | —$ONH_2(CH_3)_2$ | — | — | — |
| 4 | — | —$CH_3$ | —$OCH_3$ | — | 165–167/3mmHg | — |
| 5 | — | —$CH_3$ | —$OC_2H_5$ | — | 176–185/3mmHg | — |
| 6 | — | —$CH_3$ | —O—$C_3H_7$-(n) | — | 160–167/2mmHg | — |
| 7 | — | —$CH_3$ | —O—$C_3H_7$-(i) | — | 163–167/2mmHg | — |
| 8 | — | —$CH_3$ | —O—$C_4H_9$-(n) | — | 165–168/1mmHg | — |
| 9 | — | —$CH_3$ | —O—$C_4H_9$-(i) | — | 168–172/1mmHg | — |
| 10 | — | —$CH_3$ | —O—$C_5H_{11}$-(n) | — | 190–196/3mmHg | — |
| 11 | — | —$CH_3$ | —OCHCH$_2$CH(CH$_3$)$_2$ \| CH$_3$ | — | 168–171/1mmHg | — |
| 12 | — | —$CH_3$ | —O(CH$_2$)$_6$CH$_3$ | — | 193–196/2mmHg | — |
| 13 | — | —$CH_3$ | CH$_3$ \| —OCH$_2$CCH$_2$CH(CH$_3$)$_2$ \| CH$_3$ | — | 200–203/2mmHg | — |
| 14 | — | —$CH_3$ | C$_2$H$_5$ \| —OCH$_2$CH(CH$_2$)$_3$CH$_3$ | — | 193–196/2mmHg | — |
| 15 | — | —$CH_3$ | —O(CH$_2$)$_8$CH$_3$ | — | 205–208/2mmHg | — |
| 16 | — | —$CH_3$ | —SC$_2$H$_5$ | — | 170–173/2mmHg | — |
| 17 | — | —$CH_3$ | —OCH$_2$CH=CH$_2$ | — | 170–175/2mmHg | — |

-continued

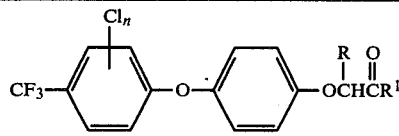

| Compound No. | $Cl_n$ | R | $R^1$ | Melting Point (°C.) | Boiling Point (°C.) | Refractive Index |
|---|---|---|---|---|---|---|
| 18 | — | —$CH_3$ | —$OCH_2C\equiv CH$ | — | 172–175/3mmHg | — |
| 19 | — | —$CH_3$ | —$OC_2H_4O$—$C_4H_9$-(n) | — | 205–208/2mmHg | — |
| 20 | — | —$CH_3$ | —$OC_2H_4OC_2H_4OC_2H_5$ | — | 207–209/2mmHg | — |
| 21 | — | —$CH_3$ | —O—(cyclohexyl-H)-$CH_3$ | — | 203–209/2mmHg | — |
| 22 | — | —$CH_3$ | —O—(phenyl)-Cl (ortho) | 84–87 | — | — |
| 23 | — | —$CH_3$ | —O—(phenyl)-Cl (para) | — | 225–231/3mmHg | — |
| 24 | — | —$CH_3$ | —O—(phenyl)-Cl,Cl | 59–61 | — | — |
| 25 | — | —$CH_3$ | —O—(phenyl)-$CH_3$ | 59–61 | — | — |
| 26 | — | —$CH_3$ | —O—(phenyl)-Cl, $CH_3$ | — | 200–207/0.2mmHg | — |
| 27 | — | —$CH_3$ | —O—(phenyl)-$CH_3O$ | 41–44 | — | — |
| 28 | — | —$CH_3$ | —O—(phenyl)-Cl, $CH_3O$ | 66–68 | — | — |
| 29 | — | —$CH_3$ | —S—(phenyl)-Cl | — | 218–226/2mmHg | — |
| 30 | — | —$CH_3$ | —$OCH_2$—(phenyl) | — | 183–185/3mmHg | — |
| 31 | — | —$CH_3$ | —$NH_2$ | 157–158 | — | — |
| 32 | — | —$CH_3$ | —$NHC_2H_5$ | 97–98 | — | — |
| 33 | — | —$CH_3$ | —$N(C_2H_5)_2$ | — | 172–176/2mmHg | — |
| 34 | — | —$CH_3$ | —$NHNH_2$ | — | — | — |
| 35 | — | —$CH_3$ | —$NHN(CH_3)_2$ | 110–112 | — | — |
| 36 | — | —$CH_3$ | —NH—(phenyl) | 129–131 | — | — |
| 37 | — | —$CH_3$ | —NH—(phenyl)-Cl | 87–89 | — | — |
| 38 | — | —$CH_3$ | —NH—(phenyl)-F | 117–119 | — | — |
| 39 | — | —$CH_3$ | —NH—(phenyl)-Br | 92–93 | — | — |
| 40 | — | —$CH_3$ | —NH—(phenyl)-Cl,Cl | 126–129 | — | — |

-continued

Structure:

$$CF_3\text{-}C_6H_3(Cl_n)\text{-}O\text{-}C_6H_4\text{-}OCHR\text{-}C(=O)R^1$$

| Compound No. | $Cl_n$ | R | $R^1$ | Melting Point (°C.) | Boiling Point (°C.) | Refractive Index |
|---|---|---|---|---|---|---|
| 41 | — | —CH₃ | —NH—(2-CH₃-C₆H₄) | 102–104 | — | — |
| 42 | — | —CH₃ | —NH—(2,5-(CH₃)₂-C₆H₃) | 101–104 | — | — |
| 43 | — | —CH₃ | —NH—(2,6-(CH₃)₂-C₆H₃) | 148–149 | — | — |
| 44 | — | —CH₃ | —NH—(3-C₂H₅-C₆H₄) | 98–103 | — | — |
| 45 | — | —CH₃ | —NH—(2-CH₃O-C₆H₄) | — | 195–205/0.2mmHg | — |
| 46 | — | —CH₃ | —NH—(3-CF₃-C₆H₄) | 126–128 | — | — |
| 47 | — | —CH₃ | —N(CH₃)(C₆H₅) | — | 220–225/2mmHg | — |
| 48 | — | —CH₃ | —N(3,4-Cl₂-C₆H₃)(CON(CH₃)₂) | — | — | — |
| 49 | — | —CH₃ | —N(3,4-Cl₂-C₆H₃)(COC₂H₅) | — | — | — |
| 50 | — | —CH₃ | —N(3,4-Cl₂-C₆H₃)(CO-cyclopropyl) | — | — | — |
| 51 | — | —CH₃ | —NHCH₂—C₆H₅ | 105–106 | — | — |
| 52 | — | —CH₃ | —NHCONH₂ | — | — | — |
| 53 | — | —CH₃ | —NHCON(CH₃)₂ | — | — | — |
| 54 | — | —CH₃ | —NHCOCH₃ | — | — | — |
| 55 | — | —CH₃ | —NH—(2-pyridyl) | — | — | — |
| 56 | — | —CH₃ | —NH—(6-CH₃-2-pyridyl) | — | — | — |

-continued

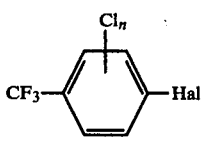

| Compound No. | Cl_n | R | R[1] | Melting Point (°C.) | Boiling Point (°C.) | Refractive Index |
|---|---|---|---|---|---|---|
| 57 | — | —CH$_3$ | —NH—N=N / N=N (triazole) | 184–186 | — | — |
| 58 | — | —CH$_3$ | —NH—(N=N / NH) | 195–197 | — | — |
| 59 | — | —CH$_3$ | —Cl | — | 135–140/2mmHg | — |
| 60 | 2-Cl* | —CH$_3$ | —OH | 90–92 | — | — |
| 61 | 2-Cl | —CH$_3$ | —ONH(C$_2$H$_4$OH)$_3$ | — | — | — |
| 62 | 2-Cl | —CH$_3$ | —O$^\ominus$(CH$_3$)$_3$N$^\oplus$C$_2$H$_4$OH | 109–115 | — | — |
| 63 | 2-Cl | —CH$_3$ | —OCH$_3$ | — | 186–189/3mmHg | — |
| 64 | 2-Cl | —CH$_3$ | —OC$_2$H$_5$ | — | 195–216/3mmHg | — |
| 65 | 2-Cl | —CH$_3$ | —OCH$_2$CH=CH$_2$ | — | 196–218/3mmHg | — |
| 66 | 3-Cl | —CH$_3$ | —OC$_2$H$_5$ | — | 183–186/2mmHg | — |
| 67 | — | —C$_2$H$_5$ | —OH | 80–81 | — | — |
| 68 | — | —C$_3$H$_7$-(i) | —OH | — | — | $n_D^{20}$ 1.505 |
| 69 | — | —C$_3$H$_7$-(n) | —OH | — | — | $n_D^{20}$ 1.511 |
| 70 | — | —C$_4$H$_9$-(n) | —OH | 68–69 | — | — |
| 71 | — | —(CH$_2$)$_5$CH$_3$ | —OH | — | — | $n_D^{20}$ 1.497 |
| 72 | — | —CH$_3$ | —N(CH$_2$CH$_2$)$_2$O (morpholino) | 116–117 | — | — |
| 73 | — | —CH$_3$ | —NHCH$_2$COOC$_2$H$_5$ | 68–69 | — | — |

*numeral designates ring position substituted

Other than the above-described compounds, an aldehyde, thioamide or amidine of α-[4-(4-trifluoromethylphenoxy)phenoxy]-propionic acid can also be expected to have sufficient herbicidal effects.

The herbicidal compound of this invention of the formula (I) can be prepared by the following method.

A p-halo-α,α,α-trifluorotoluene of the formula (II):

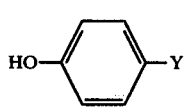

(II)

wherein Hal is a halogen atom such as a bromine, chlorine, fluorine or iodine atom with a chlorine or bromine atom being preferred, and n is the same as defined hereinabove, and a p-substituted phenol of the formula (III):

(III)

wherein Y is a hydroxy group, a (C$_1$–C$_5$)alkoxy group in which the alkyl moiety may be straight or branched chain, or a $$-OCHCR^3 \quad \text{with R above and O double-bonded}$$

group, in which R is the same as defined hereinabove and R[3] is a hydroxy group, a (C$_1$–C$_9$) alkoxy group, or an amino group, are first condensed, e.g., using an equimolar amount of the compound of the formula (II) and the compound of the formula (III), in the presence of an alkaline material to form a 4-trifluoromethyl-4'-substituted diphenyl ether of the formula (IV):

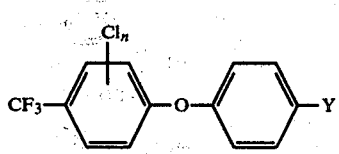

(IV)

wherein Y and n are the same as defined above. When Y is an $$-OCHCR^3$$

group, a compound of the formula (V) is obtained.

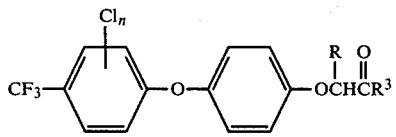 (V)

wherein R, R³ and n are the same as defined above. If desired, the resulting product of the formula (V) is treated by a conventional method to convert R³ to R¹ thereby to form the herbicidal compound of the formula (I). When Y is an alkoxy group or a hydroxy group, the resulting 4-trifluoromethyl-4′-hydroxy diphenyl ether and an α-haloalkanecarboxylic acid or a derivative thereof of the formula (VI):

 (VI)

wherein R, R³ and Hal are the same as defined above, are then condensed, e.g., using an equimolar amount of the compound of the formula (IV) and the compound of the formula (VI), in the presence of an alkaline material, with or without prior dealkylation (i.e., to remove the alkyl moiety of the alkoxy group), to form a compound of the formula (V) described above.

Examples of suitable alkaline materials which can be used in the first and second condensation reactions are alkali metal hydroxides such as sodium hydroxide or potassium hydroxide, and alkali metal carbonates such as sodium carbonate or potassium carbonate. In the first condensation, a suitable reaction temperature is at least about 100° C., preferably 100° to 200° C., and the reaction time is generally about 1 to 20 hours, preferably 1 to 10 hours. An aprotic-polar solvent, such as dimethylformamide, dimethylacetamide, dimethyl sulfoxide, N-methylpyrrolidone, hexamethylphosphoramide or sulfolane, can be used in this reaction. In the second condensation, a suitable reaction temperature is about 40° to 120° C., and the reaction time is generally about 0.5 to 10 hours. In this second condensation, a ketone such as methyl ethyl ketone or methyl isobutyl ketone can be used as a solvent.

When pyridine hydrochloride is used as a dealkylating agent in the dealkylation, the reaction temperature is desirably about 150° to 200° C., and the reaction time is most generally about 5 to 10 hours. When a hydrohalic acid such as hydrobromic acid or hydroiodic acid is used as a dealkylating agent, the dealkylating reaction is desirably carried out in the presence of a solvent of a lower fatty acid type such as acetic acid or acetic anhydride for about 5 to 10 hours at a temperature in the vicinity of the boiling point of the solvent.

The above method for production of the compounds of the formula (I) or intermediates used therein can be described in greater detail as follows:

(1) A method for preparing a compound of the formula (V):

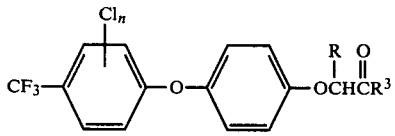 (V)

wherein R, R³ and n are the same as defined above, comprising condensing a p-halo-α,α,α-trifluorotoluene of the formula (II):

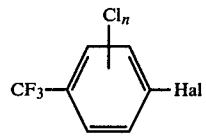 (II)

wherein Hal and n are the same as defined above, with a p-hydroxyphenoxyalkanecarboxylic acid or a derivative thereof of the formula (VII):

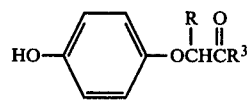 (VII)

wherein R and R³ each is as defined hereinabove, in the presence of an alkaline material at a temperature of at least about 100° C., preferably at 100° to 200° C., more preferably 130° to 180° C., for about 1 to 20 hours, preferably 1 to 10 hours.

(2) A method for preparing a compound of the formula (V):

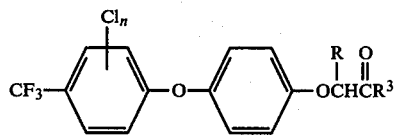 (V)

wherein R, R³ and n are the same as defined above, comprising condensing a p-halo-α,α,α-trifluorotoluene of the formula (II):

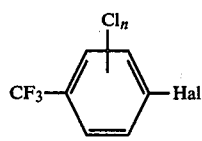 (II)

wherein Hal and n are the same as defined above, with hydroquinone in the presence of an alkaline material at a temperature of at least about 100° C., preferably 100° to 200° C., for about 1 to 20 hours to form a 4-trifluoromethyl-4′-hydroxydiphenyl ether of the following formula (VIII):

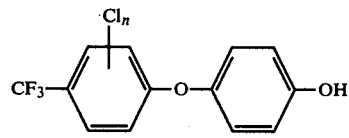 (VIII)

wherein n is the same as defined above, and then condensing the compound of the formula (VIII) with an α-haloalkanecarboxylic acid or a derivative thereof of the formula (VI):

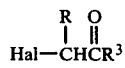 (VI)

wherein R, R³ and Hal are the same as defined above, in the presence of an alkaline material at a temperature of about 40° to 120° C., for about 0.5 to 10 hours.

(3) A method for preparing a compound of the formula (V):

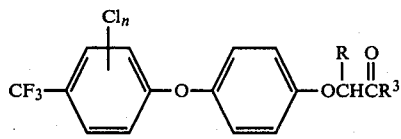

wherein R, R³ and n are the same as defined above, comprising condensing a p-halo-α,α,α-trifluorotoluene of the formula (II):

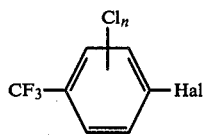

wherein Hal and n are the same as defined above, with a hydroquinone monoalkyl ether of the formula (IX):

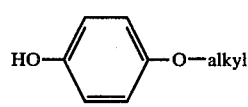

wherein "alkyl" represents an alkyl group, in the presence of an alkaline material at a temperature of at least about 100° C., preferably 100° to 200° C., more preferably 100° to 150° C., for about 1 to 20 hours, preferably 1 to 10 hours, to form a 4-trifluoromethyl-4'-alkoxydiphenyl ether of the formula (X):

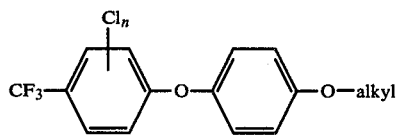

wherein "alkyl" and n are the same as defined above, dealkylating the 4-trifluoromethyl-4'-alkoxydiphenyl ether to form a 4-trifluoromethyl-4'-hydroxydiphenyl of the formula (VIII):

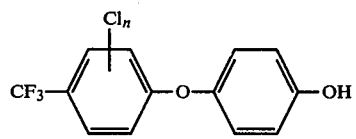

wherein n is the same as defined above, and then condensing the compound of the formula (VIII) with an α-haloalkanecarboxylic acid or a derivative thereof of the formula (VI):

wherein R, R³ and Hal are the same as defined above, in the presence of an alkaline material at a temperature of about 40° to 120° C. for about 0.5 to 10 hours. (4) An α-[4-(4-trifluoromethylphenoxy)phenoxy]alkanecarboxylic acid of the formula (Va):

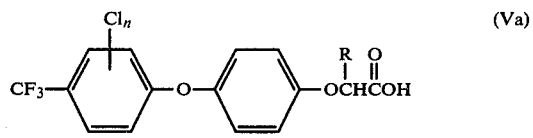

wherein R and n are the same as defined above, (the compound of the formula (V) in which R³ is a hydroxy (group) is reacted with:
(a) an alkaline material (e.g., sodium hydroxide, potassium hydroxide, ammonia, etc.) to form a salt,
(b) an alcohol (e.g., a (C₁-C₉)alcohol such as methyl alcohol, ethyl alcohol, isopropyl alcohol, tert-butyl alcohol, etc.) to form an ester,
(c) an amine (e.g., a mono- or di-(C₁-C₄)alkylamine such as methylamine, diethylamine, etc.) to form an amide,
(d) a halogenating agent (e.g., SOCl₂, PCl₃, PCl₅, POCl₃, etc.) to form a halide.

(5) An α-[4-(4-trifluoromethylphenoxy)phenoxy]alkanecarboxylic acid ester of the formula (Vb):

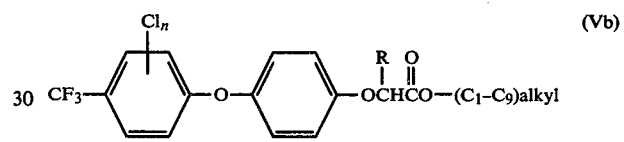

wherein R and n are the same as defined above, (the compound of the formula (V) in which R³ is a (C₁-C₉)alkoxy group), or the ester obtained by Method (4)-(b) above,
(a) is subjected to an ester-interchange reaction (e.g., using a (C₁-C₉)alcohol as described above) in the presence of a Lewis acid catalyst (such as BF₃, etc.) to form other esters,
(b) is reacted with amines (e.g., amines as described above) to form amides,
(c) is hydrolyzed (e.g., with acids or alkalis) to form acids.

(6) The halide of the formula (Vc):

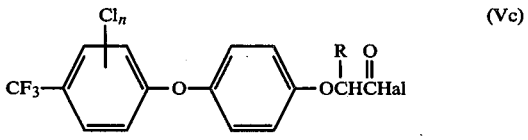

wherein R, Hal and n are the same as defined above, obtained by Method (4)-(d) above is reacted with:
(a) alcohols (e.g., a (C₁-C₉)alcohol as described above) to form esters,
(b) amines (e.g., a mono- or di-alkylamine as described above) to form amides.

Methods (4) to (6) are conventional methods and are described in, for example, Romeo B. Wagner and Harry D. Zook, *Synthetic Organic Chemistry*, John Wiley & Sons Inc., New York, London.

The herbicidal compound of this invention includes optical isomers. Thus, the herbicidal compounds obtained by the above procedures are racemic compounds, i.e., mixtures of equal amounts of a dextrorotatory compound and a levorotatory compound. If desired, the racemic compounds can be resolved using conventional techniques into dextrorotatory and levorotatory compounds. Racemic resolution methods are described in, for example, *Industrial and Engineering Chemistry*, 60, (8), 12–28. The isomers and the racemic mixture all have herbicidal activity. In general, the herbicidal activity is as follows: d-Isomer>Racemic Mixture>l-Isomer Some specific examples of preparing the herbicidal compounds of this invention are shown below. Unless otherwise indicated herein, all parts, percents, ratios and the like are by weight.

PREPARATION EXAMPLE 1

Preparation of α-[4-(4-Trifluoromethylphenoxy)phenoxy]propionic Acid 5.1 g of 4-(4-trifluoromethylphenoxy)phenol and 2.1 g of α-chloropropionic acid were heated at 80° C. with stirring, and 6.2 g of a 30% aqueous solution of sodium hydroxide was added. The reaction was carried out for 0.5 hour at 90° to 95° C. After allowing the reaction mixture to cool, the resulting solid precipitate was withdrawn, and washed with a small amount of methanol. The precipitate was dried overnight at reduced pressure to afford 5.3 g (yield: 81.5%) of the final product having a melting point of 138° to 140° C.

PREPARATION EXAMPLE 2

Preparation of α-[4-(2-Chloro-4-trifluoromethylphenoxy)phenoxy]-propionic Acid 28.9 g of 4-(2-chloro-4-trifluoromethylphenoxy)-phenol was added to 50 ml of dioxane, and with stirring at 30° to 40° C., 13.8 g of potassium carbonate was added. The mixture was heated to 40° to 60° C., and 10.8 g of α-chloropropionic acid was added. The reaction was performed for 4 hours. The disappearance of the starting phenol was confirmed by gas chromatography, and the reaction product was poured into a suitable amount of water. Sodium carbonate was added to transfer the final product into the aqueous phase. The oily phase was separated and removed, and then hydrochloric acid was added to afford 20 g of a solid precipitate. The final product obtained had a melting point of 90° to 92° C.

PREPARATION EXAMPLE 3

Preparation of Sodium α-[4-(4-Trifluoromethylphenoxy)phenoxy]propionate 32.6 g of α-[4-(4-trifluoromethylphenoxy)phenoxy]-propionic acid was dissolved in 30 ml of ethanol, and an aqueous solution of 4.0 g of sodium hydroxide in 40 ml of water was added. The mixture was maintained at 70° to 75° C. for 1 hour. Then, ethanol and water were removed from the reaction product at reduced pressure. The residue was heated at 90° C. for 4 hours to afford 34.1 g (yield: 98%) of the final product as a white solid.

PREPARATION EXAMPLE 4

Preparation of Methyl α-[4-(4-Trifluoromethylphenoxy)phenoxy]propionate 10 g of α-[4-(4-trifluoromethylphenoxy)phenoxy]propionic acid was reacted with 80 g of methanol in the presence of 5 g of boron trifluoride at 55° to 60° C. for 3 hours. The reaction product was poured into water, and extracted with chloroform. The extract was washed with dilute alkali (i.e., 2–3% NaOH aqueous solution) and water, and dried. Then, the chloroform was evaporated off. The residue was distilled at reduced pressure to afford 7.5 g of the final product having a boiling point of 165° to 167° C./3mmHg. The yield was 74%.

PREPARATION EXAMPLE 5

Preparation of Ethyl α-[4-(4-Trifluoromethylphenoxy)phenoxy]propionate (A) A solution of 73.5 g of 4-(4-trifluoromethylphenoxy)phenol and 49.2 g of ethyl α-chloropropionate and 100 g of potassium carbonate were added to 100 ml of methyl ethyl ketone, and the mixture was heated. With stirring, the reaction was performed for 10 hours at the reflux temperature (80° to 85° C.). Inorganic salts were separated from the reaction product by filtration. The filtrate was evaporated and dried. The resulting ester was extracted with chloroform, and washed with water. The chloroform was distilled off to afford 55 g of the final product (yield: 54%). The final product had a boiling point of 176° to 185° C./3 mmHg.

(B) 3.6 g of p-chloro-α,α,α-trifluorotoluene, 4.7 g of ethyl-4-hydroxyphenoxy-α-propionate and 3.3 g of potassium carbonate were mixed, and 10 ml of dimethyl sulfoxide was added to the mixture. With stirring, the reaction was performed at 120° to 130° C. for about 6 hours. The reaction product was placed in a suitable amount of water, extracted with chloroform, washed with water, and then dried with anhydrous sodium sulfate. After drying, the chloroform was evaporated off. Subsequent distillation at reduced pressure afforded 4.1 g of the final product.

PREPARATION EXAMPLE 6

Preparation of Ethyl α-[4-(2-Chloro-4-trifluoromethylphenoxy)phenoxy]-propionate:

28.9 g of 4-(2-chloro-4-trifluoromethylphenoxy)-phenol was added to 60 ml of a mixture of dioxane and dimethyl sulfoxide (1:1 by volume ratio), and with stirring at 30° to 50° C., 7.3 g of potassium hydroxide was added to form the potassium salt of the above phenol. Then, 13.7 g of ethyl α-chloropropionate was added at 40° to 50° C., and the reaction was performed for 1 hour. Completion of the reaction was confirmed by gas chromatography. The reaction product was placed in a suitable amount of water. The resulting oil settling was extracted with diethyl ether. The extract was washed with a dilute alkali solution (i.e., 2–3% NaOH aqueous solution) and water, and dried with anhydrous sodium sulfate. The ether was evaporated off, and the residue was distilled at reduced pressure to afford the final product having a boiling point of 195° to 216° C./3 mmHg.

PREPARATION EXAMPLE 7

Preparation of α-[4-(4-Trifluoromethylphenoxy)phenoxy]propionamide:

18 g of p-chloro-α,α,α-trifluorotoluene and 18 g of α-(p-hydroxyphenoxy)propionamide were dissolved in 50 ml of dimethyl sulfoxide, and 5.6 g of potassium hydroxide was added. The reaction was performed at 130° to 150° C. for about 5 hours. After the reaction, the reaction product was purified in a customary manner to afford the final product having a melting point of 157° to 158° C. The yield was 50%.

PREPARATION EXAMPLE 8

Preparation of α-[4-(4-Trifluoromethylphenoxy)phenoxy]propionanilide 34.5 g of α-[4-(4-trifluoromethylphenoxy)phenoxy]propionyl chloride synthesized by a conventional method (as described in, for example, *Synthetic Organic Chemistry*, supra) from α-[4-(4-trifluoromethylphenoxy)phenoxy]propionic acid and thionyl chloride was dissolved in 200 ml of benzene, and while maintaining the solution at 20° to 25° C., 19.5 g of aniline was added. The reaction was performed at 30° C. for 1 hour. The reaction product was poured into 300 ml of water to precipitate and washed with water, and then dried with anhydrous sodium sulfate. After drying, benzene was evaporated off, and the residue was recrystallized from a mixture of ethanol and petroleum ether (2:1 by volume) to afford 36 g of the final product having a melting point of 129° to 131° C. The yield was 90%.

The herbicidal compound of this invention can be dispersed in water to produce an aqueous dispersion. The herbicidal compound can also be formulated into various forms such as an emulsifiable concentrate, wettable powder, water-miscible solution, dust or granules by optionally incorporating conventional agriculturally acceptable adjuvants, for example, a carrier such as diatomaceous earth, calcium hydroxide, calcium carbonate, talc, white carbon, kaolin, bentonite, or Jeeklite (trade name for a zeolite, produced by Jeeklite Co.), solvents such as n-hexane, toluene, xylene, solvent naphtha, ethanol, dioxane, acetone, isophorone, methyl isobutyl ketone, dimethylformamide, dimethyl sulfoxide or water, or an anionic or nonionic surface active agent such as a sodium alkylsulfate, a sodium alkylbenzenesulfonate, sodium ligninsulfonate, a polyoxyethylene lauryl ether, a polyoxyethylene alkylaryl ether, a polyoxyethylene fatty acid ester, or a polyoxyethylene sorbitan fatty acid ester. A suitable ratio of the compound of this invention to the adjuvant(s) ranges from about 1-90:99-10 by weight, preferably 1-70:99-30 by weight.

The herbicidal composition of this invention can also be mixed or used together with suitable agricultural chemicals such as other herbicides, insecticides or fungicides, or mixed with an agricultural agent such as a fertilizer or soil conditioner or soil or sand, at the time of formulation or application. Sometimes, such a conjoint use brings about a better effect.

Some typical examples of herbicidal formulations containing the compound of this invention are shown below.

FORMULATION EXAMPLE 1

20 parts by weight of ethyl α-[4-(4-trifluoromethylphenoxy)phenoxy]propionate, 60 parts by weight of xylene and 20 parts by weight of Sorpol 2806B (trade name for a mixture of a polyoxyethylene phenyl phenol derivative, a polyoxyethylene alkylaryl ether, a polyoxyethylene sorbitan alkylate, and an alkylaryl sulfonate produced by Toho Chemical Co., Ltd.), as a surface active agent, were mixed uniformly to form an emulsifiable concentrate.

FORMULATION EXAMPLE 2

15 parts by weight of iso-propyl α-[4-(4-trifluoromethylphenoxy)phenoxy]propionate, 65 parts by weight of xylene and 20 parts by weight of polyoxyethylene stearate were mixed uniformly to form an emulsifiable concentrate.

FORMULATION EXAMPLE 3

7 parts by weight of α-[4-(4-trifluoromethylphenoxy)phenoxy]propionic acid, 58 parts by weight of bentonite, 30 parts by weight of Jeeklite, and 5 parts by weight of sodium ligninsulfonate were mixed. The mixture was granulated after addition of water in a required amount, thereby to form granules.

FORMULATION EXAMPLE 4

40 parts by weight of allyl α-[4-(2-chloro-4-trifluoromethylphenoxy)phenoxy]propionate, 55 parts by weight of Jeeklite, 2 parts by weight of a sodium alkylbenzenesulfonate and 3 parts of a mixture of equal amounts of white carbon and a polyoxyethylene alkylaryl ether were uniformly mixed, and pulverized to form a wettable powder.

FORMULATION EXAMPLE 5

3 parts by weight of N-ethyl α-[4-(4-trifluoromethylphenoxy)phenoxy]propionamide, 50 parts by weight of a powder of kaolin, 46 parts by weight of talc and 1 part by weight of Lavelin S (trade name for a sodium naphthalenesulfonate-formaldehyde condensate produced by Daiichi Kogyo Seiyaku Co., Ltd.), as a surface active agent, were mixed, and pulverized to form a dust.

FORMULATION EXAMPLE 6

20 parts by weight of sodium α-[4-(4-trifluoromethylphenoxy)phenoxy]propionate, 15 parts by weight of N-methyl-2-pyrrolidone, 5 parts by weight of a polyoxyethylene alkylaryl ether, and 60 parts by weight of ethyl alcohol were uniformly mixed to form a water-miscible solution.

The unique herbicidal activity of the herbicidal compound of this invention has already been described hereinabove, but will be described in greater detail below.

(1) The compound of this invention can be used to kill gramineous weeds by pre-emergence soil treatment or foliar treatment during the growth of weeds. In particular, the compound of this invention can be used to kill gramineous weeds which have grown to a height of about 1 meter by a foliar treatment. Since the compound of this invention is extremely safe to broad-leafed agricultural crops such as soybeans, peanuts and cotton plants, the compound is suitable for selective weed control in upland farms.

(2) If the method of application, the dosage, and the time of application are appropriately selected, for example, if a small amount of the active ingredient of this invention is applied to a field where weeds and a plant such as corn, etc. are growing, and the weeds are subjected to a foliar treatment after the plant has grown to some degree, the compound of this invention can be applied to farms where gramineous crops are cultivated. Furthermore, when the dosage of the compound is increased or the compound is used together with other herbicides, the composition can be used to kill weeds other than gramineous weeds.

(3) The compound of this invention has low toxicity to fish, and does not affect fisheries.

The herbicidal compound of this invention is most suitably applied to upland farms, especially upland farms where broad-leafed crops are cultivated, and can also be applied to orchards, forests and various non-agricultural lands. The compound of this invention can be applied as a soil treatment or a foliar treatment in upland farm conditions or under flooded conditions. A suitable rate of application varies according to various factors such as the climate condition, the soil condition, the form of the chemical, the time of application, the method of application, or the types of cultivated crops to which it is applied and the main weeds to be controlled. When the compound of this invention is used in the form of a solid preparation (e.g., dust or granules), the amount of the active ingredient is 0.1 to 1,000 g per are (100 m$^2$), preferably 1 to 700 g, and more preferably 5 to 300 g, per are.

The herbicidal activity testing of the compound of this invention and the results obtained are shown below.

TEST EXAMPLE 1

Each 1/3,000 are (1/30 m$^2$) flat was charged with soil to provide an upland condition. Predetermined amounts of seeds of edible barnyard grass, radish and soybeans were sown, and covered with soil containing seeds of large crab-grass and barnyard grass as gramineous weeds and polygonums, chickweeds the bog stichworts as broad-leafed weeds to a thickness of about 1 cm. Three days after sowing, an aqueous dispersion of each of the herbicidal compounds shown in Table 1 below was sprayed thereon, and the growth of the weeds was visually evaluated 20 days after the spraying. The results obtained are also shown in Table 1 below. The degree of growth inhibition shown in Table 1 was evaluated on a scale of 10 grades in which 10 indicates that the growth was completely inhibited and 1 indicates no inhibition.

TABLE 1

| Compound No. | Amount of Active Ingredient (g/are) | Degree of Growth Inhibition | | | |
|---|---|---|---|---|---|
| | | Edible Barnyard Grass | Radish | Soybeans | General Weeds |
| 1 | 100 | 10 | 1 | 1 | 9 |
| | 50 | 10 | 1 | 1 | 9 |
| 1' | 100 | 10 | 1 | 1 | 9 |
| | 50 | 10 | 1 | 1 | 9 |
| 2 | 100 | 10 | 1 | 1 | 9 |
| | 50 | 10 | 1 | 1 | 8 |
| 3 | 100 | 10 | 1 | 1 | 9 |
| | 50 | 10 | 1 | 1 | 8 |
| 4 | 100 | 10 | 1 | 1 | 9 |
| | 50 | 10 | 1 | 1 | 6 |
| 5 | 100 | 10 | 1 | 1 | 10 |
| | 50 | 10 | 1 | 1 | 8 |
| 6 | 100 | 10 | 1 | 1 | 9 |
| | 50 | 10 | 1 | 1 | 9 |
| 7 | 100 | 10 | 1 | 1 | 9 |
| | 50 | 10 | 1 | 1 | 6 |
| 8 | 100 | 10 | 1 | 1 | 7 |
| | 50 | 10 | 1 | 1 | 7 |
| 9 | 100 | 10 | 1 | 1 | 9 |
| | 50 | 10 | 1 | 1 | 6 |
| 10 | 100 | 10 | 1 | 1 | 6 |
| | 50 | 10 | 1 | 1 | 3 |
| 11 | 100 | 10 | 1 | 1 | 10 |
| | 50 | 10 | 1 | 1 | 8 |
| 12 | 100 | 10 | 1 | 1 | 10 |
| | 50 | 10 | 1 | 1 | 10 |
| 13 | 100 | 10 | 1 | 1 | 10 |
| | 50 | 10 | 1 | 1 | 8 |
| 14 | 100 | 10 | 1 | 1 | 6 |
| | 50 | 10 | 1 | 1 | 6 |

TABLE 1-continued

| Compound No. | Amount of Active Ingredient (g/are) | Degree of Growth Inhibition | | | |
|---|---|---|---|---|---|
| | | Edible Barnyard Grass | Radish | Soybeans | General Weeds |
| 15 | 100 | 10 | 1 | 1 | 10 |
| | 50 | 10 | 1 | 1 | 8 |
| 16 | 100 | 10 | 1 | 1 | 10 |
| | 50 | 10 | 1 | 1 | 8 |
| 17 | 100 | 10 | 2 | 1 | 10 |
| | 50 | 10 | 1 | 1 | 7 |
| 18 | 100 | 10 | 1 | 1 | 9 |
| | 50 | 10 | 1 | 1 | 7 |
| 19 | 100 | 10 | 1 | 1 | 7 |
| | 50 | 10 | 1 | 1 | 6 |
| 20 | 100 | 10 | 1 | 1 | 10 |
| | 50 | 10 | 1 | 1 | 10 |
| 21 | 100 | 10 | 1 | 1 | 10 |
| | 50 | 10 | 1 | 1 | 10 |
| 22 | 100 | 6 | 1 | 1 | 4 |
| | 50 | 5 | 1 | 1 | 4 |
| 23 | 100 | 10 | 1 | 1 | 10 |
| | 50 | 10 | 1 | 1 | 10 |
| 24 | 100 | 8 | 1 | 1 | 3 |
| | 50 | 8 | 1 | 1 | 3 |
| 25 | 100 | 10 | 1 | 1 | 5 |
| | 50 | 9 | 1 | 1 | 5 |
| 26 | 100 | 10 | 1 | 1 | 6 |
| | 50 | 9 | 1 | 1 | 6 |
| 27 | 100 | 10 | 1 | 1 | 6 |
| | 50 | 10 | 1 | 1 | 6 |
| 28 | 100 | 9 | 1 | 1 | 5 |
| | 50 | 4 | 1 | 1 | 5 |
| 29 | 100 | 10 | 1 | 1 | 10 |
| | 50 | 10 | 1 | 1 | 9 |
| 30 | 100 | 10 | 1 | 1 | 10 |
| | 50 | 10 | 1 | 1 | 10 |
| 31 | 100 | 10 | 1 | 1 | 10 |
| | 50 | 10 | 1 | 1 | 9 |
| 32 | 100 | 10 | 1 | 1 | 7 |
| | 50 | 10 | 1 | 1 | 5 |
| 33 | 100 | 10 | 1 | 1 | 4 |
| | 50 | 10 | 1 | 1 | 4 |
| 35 | 100 | 10 | 1 | 1 | 5 |
| | 50 | 10 | 1 | 1 | 5 |
| 36 | 100 | 10 | 1 | 1 | 5 |
| | 50 | 10 | 1 | 1 | 5 |
| 37 | 100 | 10 | 1 | 1 | 5 |
| | 50 | 10 | 1 | 1 | 5 |
| 39 | 100 | 5 | 1 | 1 | 3 |
| | 50 | 4 | 1 | 1 | 3 |
| 40 | 100 | 10 | 1 | 1 | 5 |
| | 50 | 10 | 1 | 1 | 5 |
| 41 | 100 | 7 | 1 | 1 | 4 |
| | 50 | 7 | 1 | 1 | 3 |
| 44 | 100 | 5 | 1 | 1 | 4 |
| | 50 | 4 | 1 | 1 | 4 |
| 45 | 100 | 8 | 1 | 1 | 5 |
| | 50 | 8 | 1 | 1 | 5 |
| 46 | 100 | 10 | 1 | 1 | 5 |
| | 50 | 10 | 1 | 1 | 5 |
| 47 | 100 | 10 | 1 | 1 | 5 |
| | 50 | 7 | 1 | 1 | 5 |
| 48 | 100 | 10 | 1 | 1 | 6 |
| | 50 | 10 | 1 | 1 | 5 |
| 50 | 100 | 10 | 1 | 1 | 5 |
| | 50 | 10 | 1 | 1 | 5 |
| 52 | 100 | 10 | 1 | 1 | 7 |
| | 50 | 10 | 1 | 1 | 6 |
| 53 | 100 | 10 | 1 | 1 | 5 |
| | 50 | 10 | 1 | 1 | 4 |
| 54 | 100 | 10 | 1 | 1 | 7 |
| | 50 | 10 | 1 | 1 | 5 |
| 55 | 100 | 10 | 1 | 1 | 7 |
| | 50 | 10 | 1 | 1 | 7 |
| 56 | 100 | 10 | 1 | 1 | 5 |
| | 50 | 9 | 1 | 1 | 5 |
| 57 | 100 | 10 | 1 | 1 | 7 |
| | 50 | 10 | 1 | 1 | 5 |
| 58 | 100 | 10 | 1 | 1 | 3 |
| | 50 | 8 | 1 | 1 | 3 |

TABLE 1-continued

| Compound No. | Amount of Active Ingredient (g/are) | Degree of Growth Inhibition | | | |
|---|---|---|---|---|---|
| | | Edible Barnyard Grass | Radish | Soybeans | General Weeds |
| 66 | 100 | 10 | 1 | 1 | 7 |
| | 50 | 10 | 1 | 1 | 6 |

TEST EXAMPLE 2

Each 1/10,000 are (1/100 m²) pot was charged with soil to provide an upland condition, and predetermined amounts of seeds of edible barnyard grass and soybeans were sown, and covered with soil to a thickness of about 1 cm. When the edible barnyard grass reached a two-leaf stage, an aqueous dispersion (concentration 1000 ppm) of each of the herbicidal compounds shown in Table 2 below was applied to foliage in a predetermined amount. Twenty days after the treatment with the chemical, the growth of the barnyard grass and soybeans was visually evaluated, and the degree of growth inhibition was evaluated on the same scale as in Test Example 1. The results obtained are shown in Table 2 below.

TABLE 2

| Compound No. | Degree of Growth Inhibition | |
|---|---|---|
| | Edible Barnyard Grass | Soybeans |
| 1 | 10 | 1 |
| 1' | 10 | 1 |
| 2 | 10 | 1 |
| 3 | 10 | 1 |
| 4 | 10 | 1 |
| 5 | 10 | 1 |
| 6 | 10 | 1 |
| 7 | 10 | 2 |
| 8 | 10 | 1 |
| 9 | 10 | 2 |
| 10 | 10 | 1 |
| 14 | 10 | 1 |
| 16 | 10 | 1 |
| 17 | 10 | 1 |
| 18 | 10 | 2 |
| 19 | 10 | 1 |
| 20 | 10 | 2 |
| 21 | 10 | 1 |
| 22 | 6 | 1 |
| 23 | 10 | 1 |
| 24 | 10 | 1 |
| 25 | 7 | 1 |
| 26 | 10 | 1 |
| 27 | 10 | 1 |
| 28 | 10 | 1 |
| 29 | 10 | 1 |
| 30 | 10 | 1 |
| 31 | 10 | 1 |
| 32 | 10 | 1 |
| 33 | 10 | 1 |
| 34 | 6 | 1 |
| 35 | 10 | 1 |
| 36 | 10 | 1 |
| 37 | 10 | 1 |
| 38 | 5 | 1 |
| 39 | 9 | 1 |
| 40 | 10 | 1 |
| 41 | 10 | 1 |
| 44 | 10 | 1 |
| 45 | 10 | 1 |
| 46 | 10 | 1 |
| 47 | 10 | 1 |
| 51 | 7 | 1 |
| 52 | 10 | 1 |
| 53 | 10 | 1 |
| 54 | 10 | 1 |

TABLE 2-continued

| Compound No. | Degree of Growth Inhibition | |
|---|---|---|
| | Edible Barnyard Grass | Soybeans |
| 55 | 10 | 1 |
| 56 | 10 | 1 |
| 57 | 10 | 1 |
| 58 | 10 | 1 |
| 60 | 10 | 2 |
| 63 | 6 | 2 |
| 64 | 6 | 2 |
| Comparison | | |
| 2,4-Dichlorophenoxyacetic Acid Dimethyl Amine Salt | 2 | 10 |
| 2,4-Dichloro-4'-nitrodiphenyl Ether | 6 | 5 |
| 2,4-Dichloro-3'-carbomethoxy-4'-nitrodiphenyl Ether | 7 | 5 |

TEST EXAMPLE 3

Each 1/10,000 are (1/100 m²) pot was charged with soil, and completely saturated with water. A predetermined amount of air-dried seeds of barnyard grass was sown, and lightly covered with soil. When the barnyard grass germinated above the ground, water was put into the pot to a depth of 3 cm to provide a flooded condition, and an aqueous dispersion of each of the herbicidal compounds shown in Table 3 was poured into the pot. Twenty days after treatment with the dispersion, the surviving barnyard grasses in the pot were pulled out, dried in air, and weighed. The percentage of the amount of surviving weeds based on the untreated pot was calculated, and the degree of growth determined. The results obtained are shown in Table 3.

TABLE 3

| Compound No. | Degree of Growth (%) | |
|---|---|---|
| | Amount of Active Ingredient (g/are) | |
| | 40 | 20 |
| 1 | 0 | 0 |
| 2 | 0 | 0 |
| 3 | 0 | 0 |
| 4 | 0 | 0 |
| 5 | 0 | 0 |
| 6 | 0 | 0 |
| 7 | 0 | 0 |
| 8 | 0 | 0 |
| 9 | 0 | 0 |
| 10 | 0 | 0 |
| 16 | 0 | 0 |
| 17 | 0 | 0 |
| 19 | 0 | 0 |
| 21 | 0 | 0 |
| 23 | 0 | 0 |
| 29 | 0 | 0 |
| 30 | 0 | 0 |
| 31 | 0 | 0 |
| 32 | 0 | 0 |
| 33 | 0 | 0 |
| 36 | 0 | 0 |
| 37 | 0 | 0 |
| 46 | 0 | 0 |
| 60 | 0 | 0 |
| 63 | 8 | 6 |
| 64 | 8 | 15 |
| 65 | 0 | 11 |
| 66 | 0 | 0 |

TEST EXAMPLE 4

Each 1/900 are (1/9 m²) pot was charged with soil to provide an upland condition. A predetermined amount of seeds of each of the crops shown in Table 4 below was sown in the pot, and covered with soil containing seeds of various weeds as shown in Table 4 below to a thickness of about 2 cm. Three days after sowing, an aqueous dispersion of each of the herbicidal compounds shown in Table 4 below was sprayed thereon in an active ingredient amount of 20 g/are. Twenty days after the spraying, the growth of the crops and the weeds were visually evaluated and the degree of growth inhibition was shown on the same scale as in Test Example 1. The results obtained are shown in Table 4 below.

TEST EXAMPLE 5

The same test as in Test Example 4 was performed except that an aqueous dispersion of each of the herbicidal compounds shown in Table 5 below was sprayed onto each of the crops at the stage of emergence in an active ingredient amount of 20 g/are. The results obtained are shown in Table 5 below.

TABLE 5

| Compound No. | Soybeans | Red Beans | Two-rowed Barley | Wheat | Peanuts | Corn | Cotton | Sunflower | Flax | Beet | Carrots | Burdock | Cucumber | Edible Barnyard Grass | Large Crab-Grass | Barnyard Grass |
|---|---|---|---|---|---|---|---|---|---|---|---|---|---|---|---|---|
| 1 | 1 | 1 | 10 | 10 | 1 | 10 | 1 | 1 | 1 | 1 | 1 | 3 | 2 | 10 | 10 | 10 |
| 2 | 1 | 2 | 10 | 10 | 1 | 10 | 1 | 1 | 2 | 1 | 1 | 1 | 2 | 10 | 10 | 10 |
| 3 | 1 | 2 | 10 | 10 | 1 | 10 | 1 | 1 | 2 | 1 | 1 | 1 | 1 | 10 | 10 | 10 |
| 4 | 3 | 2 | 10 | 10 | 1 | 10 | 1 | 5 | 3 | 1 | 1 | 1 | 3 | 10 | 10 | 10 |
| 5 | 1 | 1 | 10 | 10 | 1 | 10 | 2 | 2 | 3 | 1 | 1 | 2 | 1 | 10 | 10 | 10 |
| 19 | 3 | 3 | 10 | 10 | 1 | 10 | 1 | 1 | 3 | 1 | 1 | 2 | 1 | 10 | 10 | 10 |
| 31 | 1 | 1 | 10 | 10 | 1 | 10 | 1 | 1 | 1 | 1 | 1 | 1 | 1 | 10 | 10 | 10 |
| 32 | 1 | 1 | 10 | 10 | 1 | 10 | 1 | 1 | 1 | 1 | 1 | 1 | 1 | 10 | 10 | 10 |
| 60 | 1 | 1 | 9 | 10 | 1 | 10 | 1 | 1 | 2 | 1 | 1 | 2 | 1 | 10 | 10 | 10 |
| 63 | 4 | 1 | 10 | 10 | 1 | 10 | 1 | 3 | 2 | 1 | 1 | 1 | 1 | 10 | 10 | 10 |

TEST EXAMPLE 6

In a field for cotton and peanuts, an area of about 50 m² was used as one test area, and the testing was carried

TABLE 4

| Compound No. | Soybeans | Red Beans | Two-rowed Barley | Wheat | Peanuts | Corn | Cotton | Sunflower | Flax | Beet | Lettuce | Eggplant |
|---|---|---|---|---|---|---|---|---|---|---|---|---|
| 1 | 1 | 1 | 9 | 10 | 1 | 9 | 1 | 1 | 1 | 1 | 1 | 1 |
| 2 | 1 | 1 | 10 | 10 | 1 | 10 | 1 | 1 | 1 | 1 | 1 | 1 |
| 3 | 1 | 1 | 10 | 10 | 1 | 10 | 1 | 1 | 1 | 1 | 1 | 1 |
| 4 | 1 | 1 | 10 | 10 | 1 | 10 | 1 | 1 | 1 | 1 | 1 | 1 |
| 5 | 1 | 1 | 10 | 10 | 1 | 9 | 1 | 1 | 1 | 1 | 1 | 1 |
| 6 | 1 | 1 | 10 | 10 | 1 | 10 | 1 | 1 | 1 | 1 | 1 | 1 |
| 7 | 1 | 1 | 10 | 10 | 1 | 10 | 1 | 1 | 1 | 1 | 1 | 1 |
| 8 | 1 | 1 | 10 | 10 | 1 | 10 | 1 | 1 | 1 | 1 | 1 | 1 |
| 9 | 1 | 1 | 10 | 10 | 1 | 10 | 1 | 1 | 1 | 1 | 1 | 1 |
| 10 | 1 | 1 | 10 | 10 | 1 | 10 | 1 | 1 | 1 | 1 | 1 | 1 |
| 17 | 1 | 1 | 10 | 10 | 1 | 10 | 1 | 1 | 1 | 1 | 1 | 1 |
| 19 | 1 | 1 | 7 | 10 | 1 | 10 | 1 | 1 | 1 | 1 | 1 | 1 |
| 23 | 1 | 1 | 9 | 10 | 1 | 10 | 1 | 1 | 1 | 1 | 1 | 1 |
| 31 | 1 | 1 | 6 | 8 | 1 | 7 | 1 | 1 | 1 | 1 | 1 | 1 |
| 32 | 1 | 1 | 6 | 10 | 1 | 8 | 1 | 1 | 1 | 1 | 1 | 1 |
| 60 | 1 | 1 | 4 | 4 | 1 | 4 | 1 | 1 | 1 | 1 | 1 | 1 |
| 63 | 1 | 1 | 6 | 10 | 1 | 10 | 1 | 1 | 1 | 1 | 1 | 1 |
| 66 | 1 | 1 | 3 | 7 | 1 | 6 | 1 | 1 | 1 | 1 | 1 | 1 |

| Compound No. | Green Onions | Spinach | Cabbage | Radish | Tomatoes | Carrots | Burdock | Cucumber | Edible Barnyard Grass | Large Crabgrass | Barnyard Grass |
|---|---|---|---|---|---|---|---|---|---|---|---|
| 1 | 1 | 1 | 1 | 1 | 1 | 1 | 1 | 1 | 10 | 10 | 10 |
| 2 | 1 | 1 | 1 | 1 | 1 | 1 | 1 | 1 | 10 | 10 | 10 |
| 3 | 1 | 1 | 1 | 1 | 1 | 1 | 1 | 1 | 10 | 10 | 10 |
| 4 | 1 | 1 | 1 | 1 | 1 | 1 | 1 | 1 | 10 | 10 | 10 |
| 5 | 1 | 1 | 1 | 1 | 1 | 1 | 1 | 1 | 10 | 10 | 10 |
| 6 | 1 | 1 | 1 | 1 | 1 | 1 | 1 | 1 | 10 | 10 | 10 |
| 7 | 1 | 1 | 1 | 1 | 1 | 1 | 1 | 1 | 10 | 10 | 10 |
| 8 | 1 | 1 | 1 | 1 | 1 | 1 | 1 | 1 | 10 | 10 | 10 |
| 9 | 1 | 1 | 1 | 1 | 1 | 1 | 1 | 1 | 10 | 10 | 10 |
| 10 | 1 | 1 | 1 | 1 | 1 | 1 | 1 | 1 | 10 | 10 | 10 |
| 17 | 1 | 1 | 1 | 1 | 1 | 1 | 1 | 1 | 10 | 10 | 10 |
| 19 | 1 | 1 | 1 | 1 | 1 | 1 | 1 | 1 | 10 | 10 | 10 |
| 23 | 1 | 1 | 1 | 1 | 1 | 1 | 1 | 1 | 10 | 10 | 10 |
| 31 | 1 | 1 | 1 | 1 | 1 | 1 | 1 | 1 | 10 | 10 | 10 |
| 32 | 1 | 1 | 1 | 1 | 1 | 1 | 1 | 1 | 10 | 10 | 10 |
| 60 | 1 | 1 | 1 | 1 | 1 | 1 | 1 | 1 | 10 | 9 | 9 |
| 63 | 1 | 1 | 1 | 1 | 1 | 1 | 1 | 1 | 10 | 10 | 10 |
| 66 | 1 | 1 | 1 | 1 | 1 | 1 | 1 | 1 | 10 | 10 | 10 | out using varying amounts of each of the herbicidal compounds shown in Table 6 below. In each test area, the crops were grown for 60 days after sowing, and gramineous weeds such as large crab-grass, barnyard grass and pigeon grass as main weeds had grown to a height of 20 to 30 cm. Broad-leafed weeds such as pale smartweeds and beggar-ticks were also growing.

25 g, 50 g or 75 g of a 20% emulsifiable concentrate in accordance with the formulation in Formulation Example 1 above was diluted with 5 liters of water, and each of the compositions was sprayed onto the plants from above. In the area to which the composition containing the compound of the present invention had been applied, decay of the weeds near the ground and the nodular parts was observed about 7 days after spraying, and the weeds began to drop and turn yellow entirely. On the 15th day, all of the weeds had withered and died. However, no phytotoxicity to cotton and peanut plants was observed. The results obtained are shown in Table 6. The evaluation grades in Table 6 are on the same scale as in Test Example 1.

TABLE 6

| Compound No. | Amount of Active Ingredient (g/are) | Degree of Growth Inhibition | | | | | | |
|---|---|---|---|---|---|---|---|---|
| | | Cotton | Peanuts | Large Crab-grass | Barnyard Grass | Pigeon Grass | Pale Smart-weed | Beggar-ticks |
| 5 (invention) | 30 | 1 | 1 | 10 | 10 | 10 | 2 | 2 |
| | 20 | 1 | 1 | 10 | 10 | 10 | 1 | 1 |
| | 10 | 1 | 1 | 10 | 10 | 10 | 1 | 1 |
| Ethyl α-[4-(4-Chloro-phenoxy)phenoxy-propionate (comparison) | 30 | 1 | 1 | 8 | 7 | 8 | 1 | 1 |
| | 20 | 1 | 1 | 6 | 7 | 7 | 1 | 1 |
| | 10 | 1 | 1 | 3 | 4 | 4 | 1 | 1 |

While the invention has been described in detail and with reference to specific embodiments thereof, it will be apparent to one skilled in the art that various changes and modifications can be made therein without departing from the spirit and scope thereof.

What is claimed is:

1. A compound having the formula:

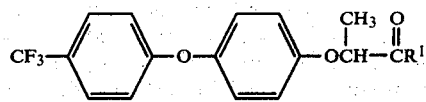

wherein $R^1$ is an n-butoxyethoxy group or an ethoxyethoxyethoxy group.

2. The compound of claim 1, wherein $R^1$ is an n-butoxyethoxy group.

3. The compound of claim 1, wherein $R^1$ is an ethoxyethoxyethoxy group.

4. A herbicidal composition comprising a herbicidally effective amount of the compound as defined in claim 1 as an active ingredient and an agriculturally acceptable adjuvant.

5. A method for controlling noxious weeds in the presence of cultivated crops, which comprises applying a herbicidally effective amount of the herbicidally composition as defined in claim 4 to an upland area where the cultivated crops are growing.

6. A method for selectively controlling gramineous weeds in the presence of broad-leafed crops, which comprises applying a herbicidally effective amount of the herbicidal composition as defined in claim 4 to an upland area where the broad-leafed corps are growing, thereby to kill gramineous weeds selectively by withering.

* * * * *